(12) United States Patent
Lee (10) Patent No.: US 8,960,650 B2
(45) Date of Patent: Feb. 24, 2015

(54) MULTIFUNCTIONAL SCHUMANN WAVE MACHINE

(76) Inventor: Chung-Ming Lee, Taichung (TW)

( * ) Notice: Subject to any disclaimer, the term of this patent is extended or adjusted under 35 U.S.C. 154(b) by 491 days.

(21) Appl. No.: 13/487,571

(22) Filed: Jun. 4, 2012

(65) Prior Publication Data

US 2013/0175361 A1    Jul. 11, 2013

(30) Foreign Application Priority Data

Jan. 6, 2012 (TW) .............................. 101200352 U
Jan. 6, 2012 (TW) .............................. 101200354 U (51) Int. Cl.
  *B01F 3/04*   (2006.01)
(52) U.S. Cl.
  USPC ................ 261/78.2; 261/81; 261/83; 261/84; 261/119.1; 261/123; 261/DIG. 65
(58) Field of Classification Search
  USPC ................... 261/78.2, 81, 83, 84, 119.1, 123, 261/DIG. 65
  See application file for complete search history.

(56) References Cited

FOREIGN PATENT DOCUMENTS

JP    08024501 A  *  1/1996

* cited by examiner

*Primary Examiner* — Robert A Hopkins
(74) *Attorney, Agent, or Firm* — Muncy, Geissler, Olds & Lowe, P.C.

(57) ABSTRACT

A multifunctional Schumann wave machine of the present invention includes a shell, a luminous device, a rotary device, a rotary blade, a droplets straining device and an air blower. The present invention provides color therapy as its luminous bodies emit lights to outside of the shell and release Schumann waves. The rotary blade and droplets straining device can produce and spray fine droplets with anions. Additionally, the water contained in the present invention is added some aromatic essential oil. Bodies and minds of users are relaxed and happy in the fresh and clean environment which is full of sunlight, air and water.

9 Claims, 8 Drawing Sheets

MULTIFUNCTIONAL SCHUMANN WAVE MACHINE

BACKGROUND OF THE INVENTION

1. Field of the Invention

The present invention relates to an atomizing apparatus.

2. Description of the Prior Art

In the modern society, the growths of economic and technology advance by leaps and bounds. Although it brings human beings to lead a convenient and efficient life, the working time extends so long and the life is so rush that bodies and minds of human beings become ill.

There are many kinds of conventional atomizing apparatuses, ones only can produce droplets with anions for convalescing and relaxing bodies and minds of users, and the other ones only can produce droplets with aromatic essential oil for spraying into the air, cleansing the environment, and relaxing bodies and minds of users. If users would like to create an environment full of anions and aromatic essential oil, they have got to buy two kinds of atomizing apparatuses. They would spend much money on the atomizing apparatuses, and the atomizing apparatuses would occupy much space as well.

Moreover, the conventional atomizing apparatuses include a high-frequency shaker generating high-frequency vibration to vibrate the water around the shaker, so that the water turns into droplets. Further, the droplets are blown up and suspended in the ambient environment by an electrical fan or the like. However, the droplets produced by the conventional atomizing apparatuses are too large and the number of anions attached on the droplets is too less. No matter which kinds of the atomizing apparatuses, all of them emphasize on relaxing users' sense of smell. As for convalescent or atmosphere of the sense of sight is not emphasized.

The present invention is, therefore, arisen to obviate or at least mitigate the above mentioned disadvantages.

SUMMARY OF THE INVENTION

The main object of the present invention is to provide a multifunctional Schumann wave machine, which produces and sprays fine mist with anions and aromatic essential oil and emits colored lights for creating atmosphere at nighttime and relaxing bodies and minds of users.

To achieve the above and other objects, a multifunctional Schumann wave machine of the present invention includes a shell, a luminous device, a rotary device, a rotary blade, a droplets straining device and an air blower.

The shell is formed with a receiving space for storaging water therein. The shell is formed with an air intake channel and an exhaust channel. The air intake channel and the exhaust channel communicate to the receiving space respectively. The exhaust channel has a tubular space. The shell has an annular baffle.

The luminous device is disposed around the shell. Lights generated by the luminous device emits towards outside of the shell. Preferably, the luminous device comprises a plurality of luminous bodies, each of which is light-emitting diode.

The rotary device is disposed in the shell firmly.

The rotary blade is disposed on the rotary device used for driving the rotary blade to rotate. The rotary blade is located in the receiving space, and the baffle surrounds the rotary blade, so that the water in the receiving space is sprayed radially by the surface of the plate of the rotary blade and strikes against the baffle to produce droplets with anions.

The droplets straining device is received in the tubular space and adapted for producing and spraying extremely fine mist.

The air blower is disposed in the shell firmly. The air blower is used for driving air via the air intake channel into the receiving space and then via the exhaust channel away from the receiving space, so that the air and the atomized water flows through the droplets straining device to outside of the shell.

The multifunctional Schumann wave machine of the present invention provides color therapy as its luminous bodies emit lights to outside of the shell and release Schumann waves. The rotary blade and droplets straining device can produce and spray fine droplets with anions. Additionally, the water contained in the present invention is added some aromatic essential oil. Bodies and minds of users are relaxed and happy in the environment which is full of sunlight (LED lights), fresh air (aromatic essential oil) and water (atomized droplets with anions).

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Please refer to FIG. 1 to FIG. 6 for a preferred embodiment of the present invention. The multifunctional Schumann wave machine of the present embodiment comprises a shell, an air blower 2, an atomizing device 3, a rotary device 4, a rotary blade 5, a droplets straining device 6 and a luminous device.

Figure 1:
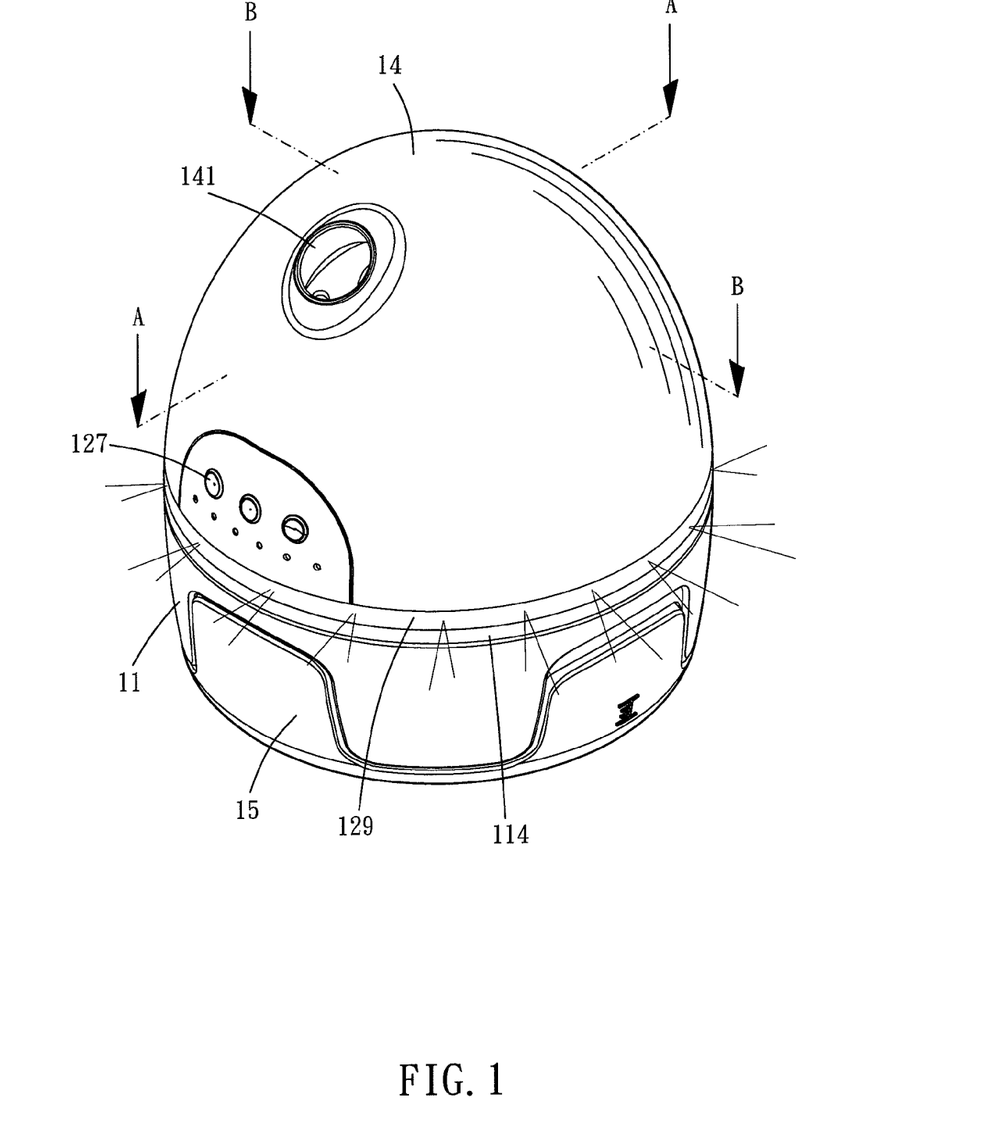
FIG. 1 is a stereogram showing the present invention.
Figure 2:
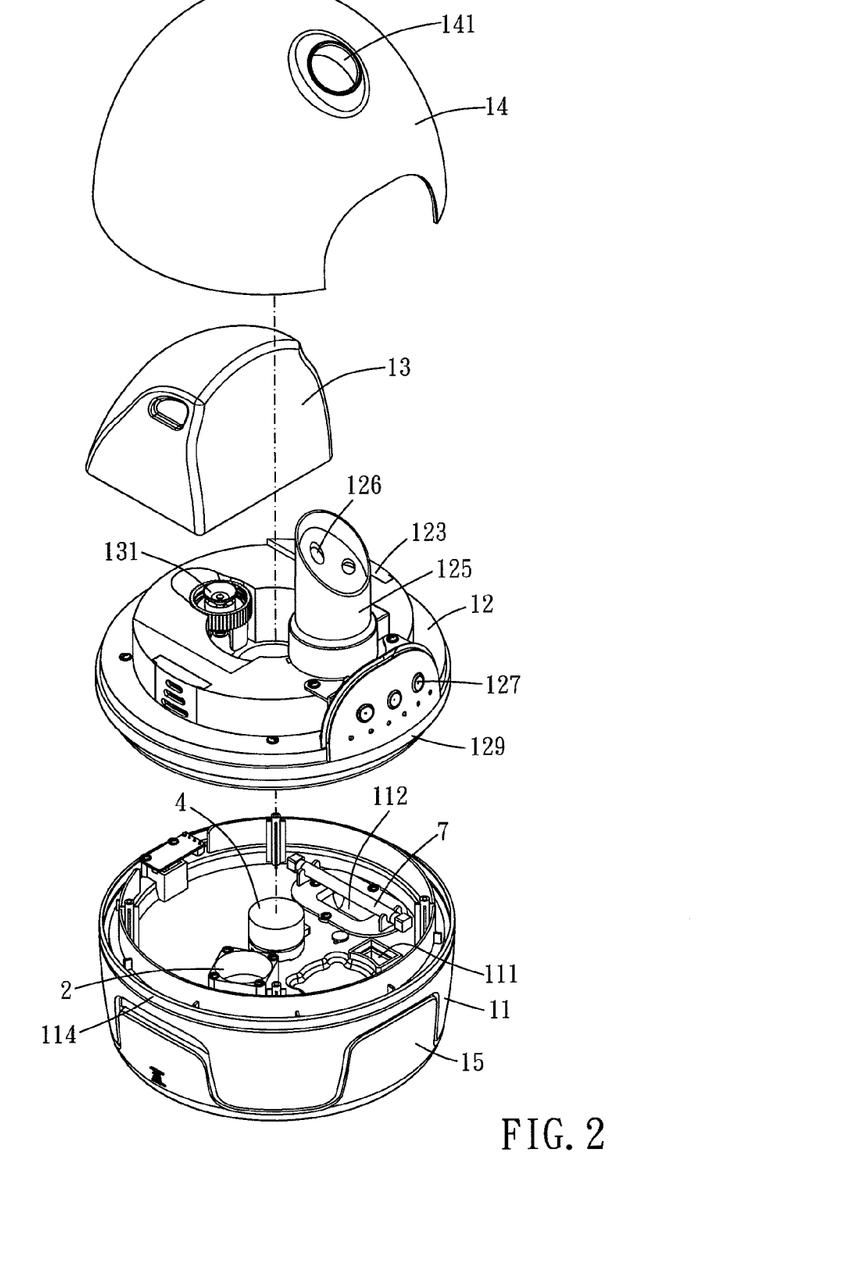
FIG. 2 is a breakdown drawing showing the present invention.

Please refer to FIG. 2, the shell includes a base 11, a laminate 12, a tank 13, and an outer housing 14. The shell further has a bottom housing 15 under the base 11. After assembling the bottom housing 15, the base 11, the laminate 12, the tank 13, and the outer housing 14 in turn, the shell to be completely installed, and the shell is formed with a receiving space therein. The receiving space further is divided into several rooms by the base 11, the laminate 12, and the tank 13. An outer periphery of a top portion of the base 11 and an outer periphery of the laminate 12 define a luminous space 16, as shown in FIG. 5A. The luminous space 16, preferably, does not communicate with other rooms, i.e. the luminous space 16 is isolated from other rooms, so that water does not run into the luminous space 16 from other rooms.

The bottom housing 15 is detachably assembled to the base 11 and is used for containing water in the room between the bottom housing 15 and the base 11. Wherein the amount of water preferably is less than or equals to one half of the room, so that the room still has some dead space.

The base 11 is formed with two openings 111 and a transparent window 112. And the air blower 2, the rotary device 4, and an ultraviolet lamp 7 are disposed in the base 11 firmly. Wherein the air blower 2 corresponds to one of the openings 111, the other opening 111 keeps opening freely. The ultraviolet lamp 7 corresponds to the transparent window 112, so that the ultraviolet lamp towards the room between the base 11 and the bottom housing 15 emits ultraviolet ray through the transparent window 112 into the room. Please refer to FIG. 5 and FIG. 6, the base 11 has an annular baffle 113 protruding from the base 11 and located between the base 11 and the bottom housing 15. Besides, the outer periphery of the top of the base 11 is formed with a first annular light transmissive portion 114.

Figure 3:
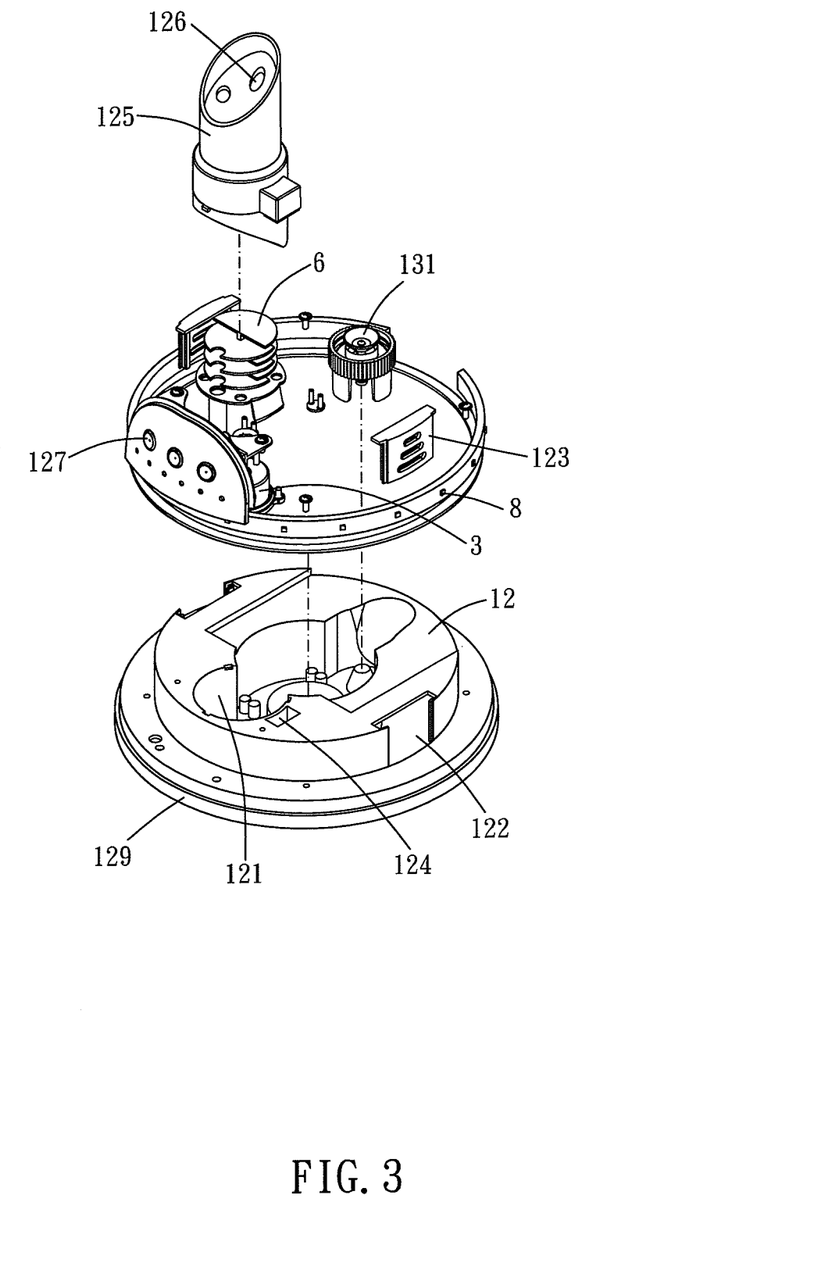
FIG. 3 is a partial breakdown drawing showing the present invention.
Figure 4:
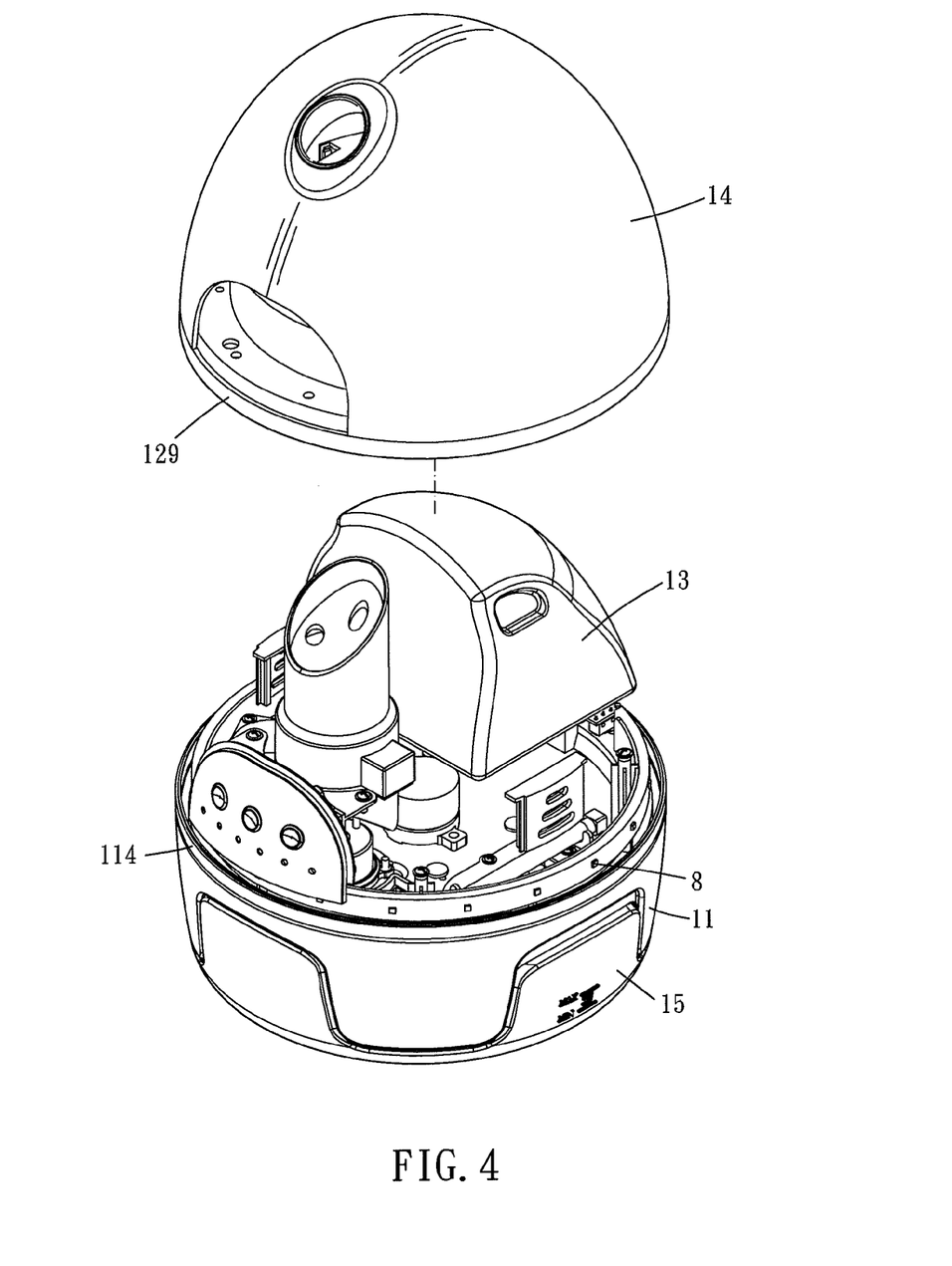
FIG. 4 is a diagram showing an outer housing being lifted up from a base.

Please refer to FIG. 2 to FIG. 5, the laminate 12 is disposed on the base 11. The atomizing device 3 is disposed on the laminate 12 firmly. As shown in FIG. 3, the surface of the laminate 12 is formed with a concave groove 121. The atomizing device is located the lower part of the concave groove 121, so that the concave groove 121 may contain water. The water can flow towards the lower part of the concave groove 121 into the atomizing device 3 spontaneously. The laminate 12 is formed with an opening hole 122 communicating a room of an upper side of the laminate 12 to a room of a lower side of the laminate 12. Preferably, a filter plate 123 or other similar filtration devices drawably disposed in the opening hole 122 are used for filtrating the dust carried by air which flows through the opening hole 122. The laminate 12 is formed with an opening 124 communicating with the openfreely opening 111 of the base. In this way, the air from the room between the base 11 and the bottom housing 15 flows through the opening 111 of the base 11 and the opening 124 of the laminate into the upper side of the laminate 12. The laminate 12 has an exhaust cylinder 125 thereon. A bottom of the exhaust cylinder 125 covers upon the atomizing device 3 and the opening 124 of the laminate 12. A top of the exhaust cylinder 125 is formed with a pore 126, so that the exhaust cylinder 125 is formed with an exhaust channel. The exhaust channel has a tubular space. The laminate 12 further has a controlling button 127 or a panel used for controlling each element of the present invention on and off or controlling each element's working efficiency. The outer periphery of the laminate 12 is formed with a second annular light transmissive portion 129.

The tank 13 disposed on the laminate 12 includes a valve 131 receiving in the concave groove 121. The tank 13 contains water. The water can flow through the valve 131 into the concave groove 121 of the laminate. Wherein the valve 131 is able to be turned on and off as the amount of water in the concave groove 121, so as to avoid too much water from the tank 13 filling into the concave groove 121 and overflowing the concave groove 121.

The outer housing 14 disposed on the laminate 12 is formed with an opening 141 corresponding to the pore 126 of the top of the exhaust cylinder 125, so that the air of the receiving space of the shell exhausts outwardly via the exhaust channel and the opening 141. Please refer to FIG. 5, the outer housing 14 is formed with several air inlets 142 called air intake channels. The air inlets 142 directly communicate with the room between the outer housing 14 and the laminate 12, so that the outside air may flow through the air inlets 142 into the receiving space of the shell.

Please refer to FIG. 2 to FIG. 5, the air blower 2 disposed in the shell firmly is used for driving air via the air intake channel into the receiving space and then via the exhaust channel away from the receiving space. More specifically, the air blower 2 is disposed in the base 11. When the air blower is turned on, the air between the base 11 and the laminate 12 would be sent into the room between the base 11 and the bottom housing 15. At the present time, the outside air flows through the air inlets 142 of the outer housing, the room between the outer housing 14 and the laminate 12, and the opening 122 of the laminate 12 into the room between the base 11 and the laminate 12. The air in the room between the base 11 and the bottom housing 15 is pushed and flows through the opening 111 of the base 11 and the opening 124 of the laminate 12, which correspond to each other, into the exhaust cylinder 125 and then via the exhaust channel to outside of the shell.

The atomizing device 3 is disposed on the laminate 12. When the atomizing device 3 is turned on, it would generate high-frequency vibration to vibrate and atomize the water contacting the atomizing device 3 into droplets. The droplets would suspend upwardly in the air so the exhaust cylinder 125 is full of droplets. When the air exhausts to outside of the shell outwardly, the droplets would flow out to outside of the shell with the air. Wherein the atomizing device 3 further has a sensor 31 extending upwardly. The sensor 31 is used for determining the water level. When the atomizing device 3 is immersed in the water and the water level rises up to a predetermined level of the atomizing device 3, the sensor 31 would turn off the atomizing device 3.

The rotary device 4 disposed in the base 11 is used for providing a rotary power. More definitely, the rotary device 4 is a motor or the like and includes gear assembly or other similar rotational speed adjustable mechanisms.

The rotary blade 5 is disposed on the rotary device 4 used for driving the rotary blade 5 to rotate. Please refer to FIG. 5 to FIG. 9, the rotary blade 5 has a rotation axle 51 and a plate 52. The plate 52 extends from the rotation axle 51 radially. The plate 52 has an outer periphery tortuously formed with one or more radial recesses 53. In this embodiment, the outer periphery is formed with five radial recesses 53. The radial recesses 53 surround the rotation axle 51 and arrange on the outer periphery circularly. Preferably, the radial recesses 53 arrange on the outer periphery circularly and equidistantly, so that the plate 52 is formed with plural wings. Each wing is located between two adjacent radial recesses. The plate 52 is formed with a plurality of peaks and a plurality of valleys. The peaks and the valleys extend radially and arrange circularly, so that the plate 52 is axially curved and formed in a wave shape. A top of the rotation axle 51 is installed on the rotary device 4, and a bottom of the rotation axle 51 extends from the plate 52 axially and narrows down gradually. The bottom of the rotation axle 51 inserts to the water contained in the bottom housing 15. Also, the bottom of the rotation axle 51 is hollow so as to lose its weight. The rotary blade 5 is located in the room between the base 11 and the bottom housing 15. And the baffle 113 of the base surrounds the rotary blade 5. More specifically, the baffle 113 surrounds the plate 52.

The water contained in the bottom housing 15 is thrown and sprayed by said rotary device 4 and rotary blade 5. And then the water strikes against the baffle 113. Thereafter, the water mist or the droplets are generated and carry the anions. When the rotary device 4 drives the rotary blade 5 to rotate, due to the water contained in the bottom housing 15, especially in contact with the bottom of the rotation axle 51, is influenced by the effect of centrifugal force and its adhesion force, so that the water is moved along the surface of the rotation axle 51 to the surface of the plate 52, and further is sprayed radially by the surface of the plate 52 and strikes against the baffle 113. The water contained in the bottom housing 15 is stricken continuously and then falls down like a waterfall. Afterwards the present invention produces water mist or droplets with anions in the room between the base 11 and the bottom housing 15. The air driven by the air blower 2 carries the water mist or the droplets to the exhaust cylinder 125, and further flows to outside of the shell together.

Please refer to FIG. 3 to FIG. 6, the droplets straining device 6 comprises a rod 61 and a division plate assembly. The division plate assembly extends from the rod 61 radially. The droplets straining device 6 is disposed in the exhaust cylinder 125 firmly. Preferably, the droplets straining device 6 can assemble with and detach from the exhaust cylinder 125 so the droplets straining device 6 is received in the tubular space of the exhaust cylinder 125. An outer periphery of the division plate assembly away from the rod 61 abuts a periphery of the tubular space and defines the tubular space into a gas channel, so that the air flowed through the exhaust cylinder 125 or the exhaust channel have to flow through the gas channel of the droplets straining device 6. Wherein the gas channel is curved in shape and extends non-linearly. Thereby an extending length of the gas channel longer than a length of the tubular space.

Figure 5:
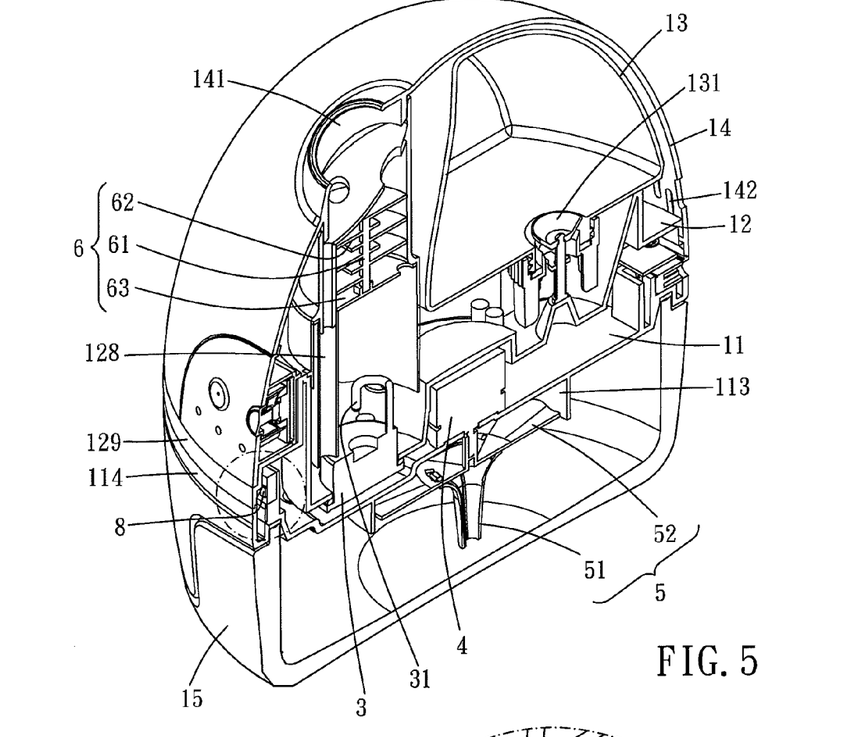
FIG. 5 is an AA cross-section view of FIG. 1.
Figure 5A:
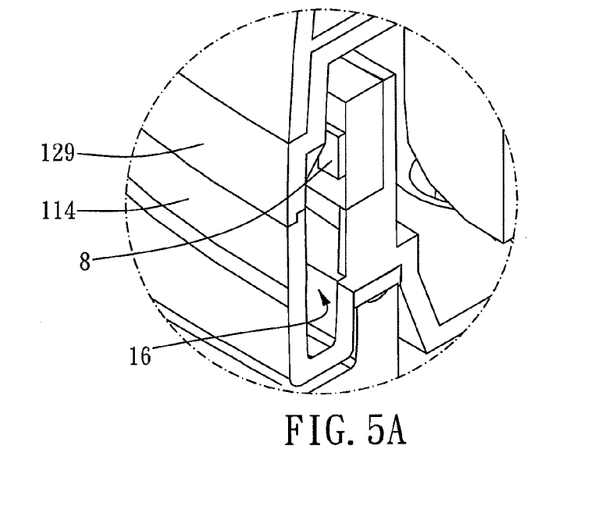
FIG. 5A is a partial enlargement view of FIG. 5.
Figure 6:
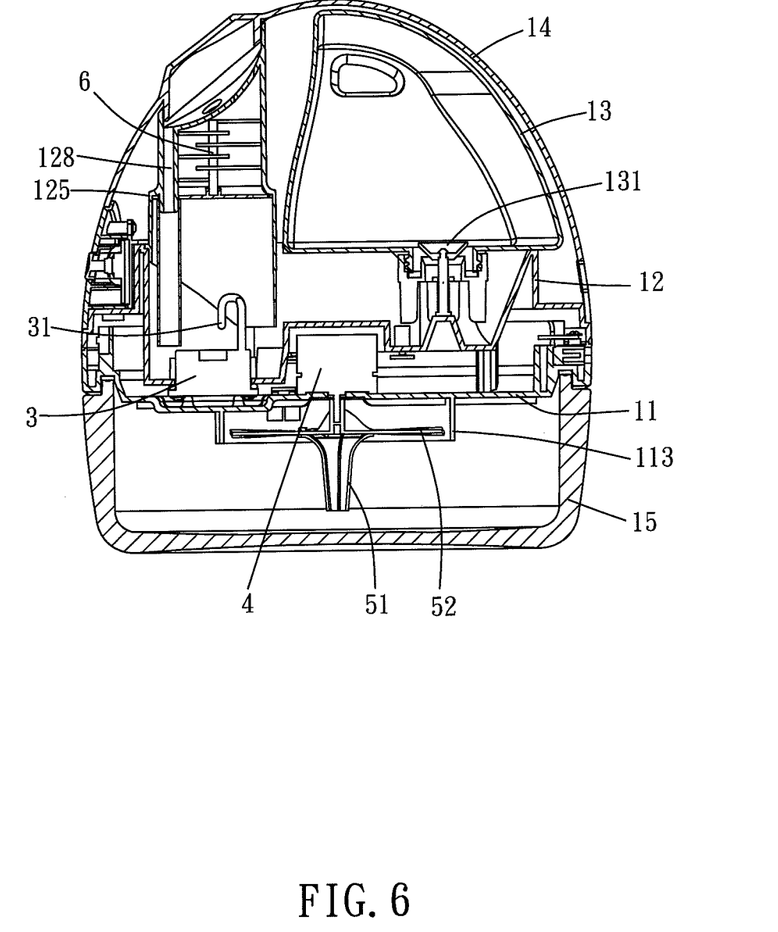
FIG. 6 is an AA side cross-section view of FIG. 1.
Figure 7:
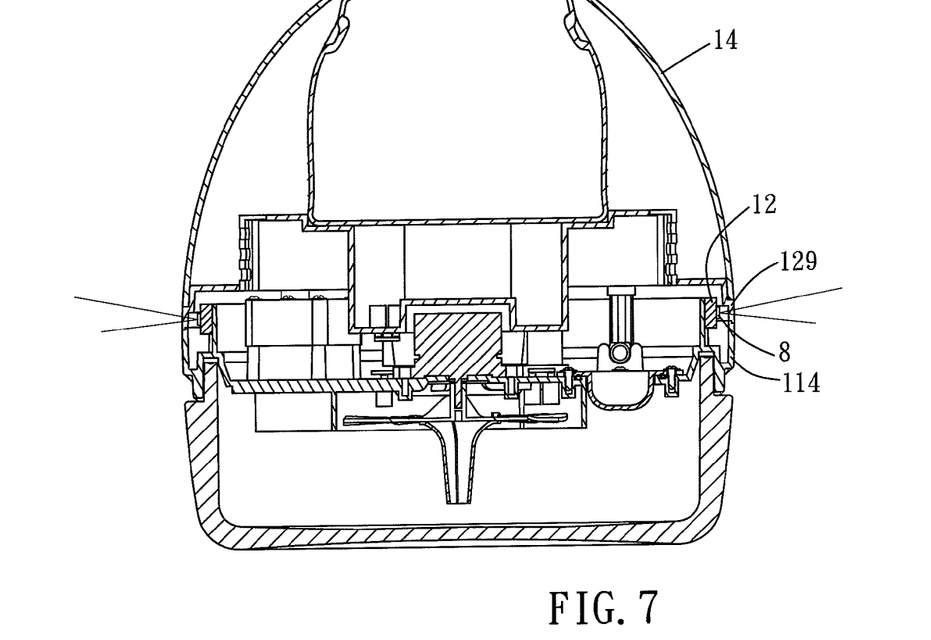
FIG. 7 is a BB side cross-section view of FIG. 1.
Figure 7A:
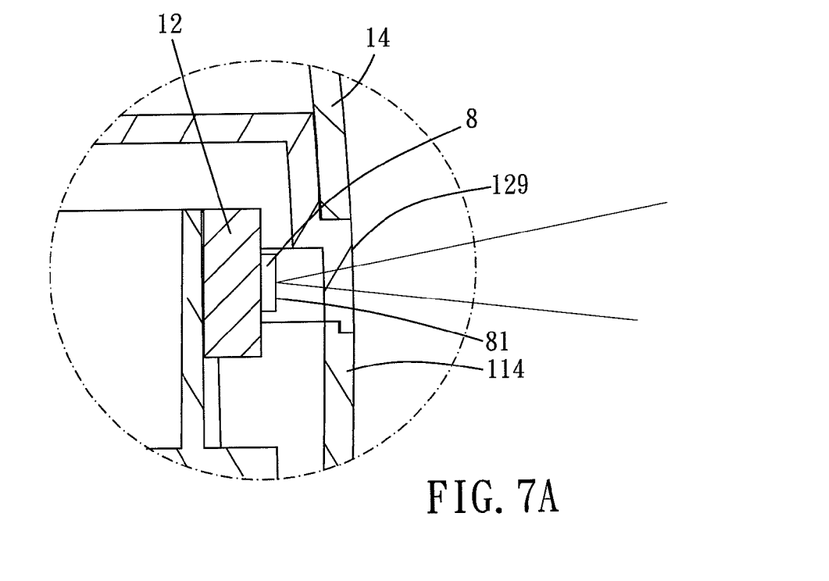
FIG. 7A is a partial enlargement view of FIG. 7.
Figure 10:
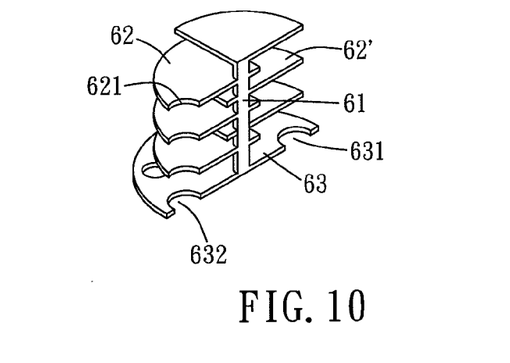
FIG. 10 is a cross-section showing a droplets straining device.

More clearly, please FIG. 5 and FIG. 10, in this embodiment, the division plate assembly of the droplets straining device 6 comprises a plurality of division plates 62 and 62'. The division plates 62 and 62' respectively extend from the rod 61 radially so that the tubular space, which is the droplets straining device 6 therein, is divided into plural compartments. One side of each of the division plates 62 and 62' is formed with an opening. Any two adjacent compartments are communicated with each other by the opening therebetween. Wherein for curving the gas channel, the positions of the openings of two adjacent the division plates 62 and 62' are staggered to each other. In other words, the openings of any two adjacent division plates 62 and 62' do not overlap and intersect with each other when looking at the division plate assembly from an orientation parallel to the rod 61. Preferably, the openings of any two adjacent division plates 62 and 62' are further away from each other, so that the air is blocked by the division plates 62 and 62' and the positions of the openings of the division plates 62 and 62'. The air cannot flow through the openings of two adjacent division plates 62 and 62' linearly. In this embodiment, the opening of each of division plates 62 and 62' is semicircular in shape. Wherein due to the division plates 62 and 62' have to be disposed on the rod 61 and stagger to adjacent division plates for blocking the openings, the specific figure of each opening of the division plates 62 and 62' is bow-shaped and smaller than a semicircle.

The droplets straining device 6 comprises a bottom plate 63 extending from a bottom of the rod radially. An outer periphery of the bottom plate 63 abuts the periphery of the tubular space. The bottom plate 63 is formed with plural openings 631 communicating between the space under the bottom plate 63 and the gas channel divided by the division plate assembly. In addition, please refer to FIG. 4, in this embodiment, the exhaust cylinder has a tube 128. The condensed water on the top of the exhaust cylinder 125 flows through the tube 128 into the concave groove 121 of the laminate 12 to recycle the condensed water. The droplets straining device 6 is formed with plural concave holes 621 and 632 on some division plates 62 and the bottom plate 63. The concave holes 621 and 632 correspond to the tube 128.

Please refer to FIG. 5 and FIG. 5A, the luminous device comprises a plurality of luminous bodies 8, which are disposed around inside of the outer periphery of the laminate 12 and located in the luminous space 16. Please refer to FIG. 7 and FIG. 7A, each of the luminous bodies 8 has a luminous end 81. The luminous end 81 faces the first and the second annular light transmissive portions 114, 129, so that lights generated by each luminous body 8 emit annularly through the first and the second annular light transmissive portions 114, 129 to outside of the shell. Preferably, the luminous bodies 8 are light-emitting diode lamps or strips.

The use of said device, please refer to FIG. 2 to FIG. 6, the present invention provides users to contain water with the tank 13 and the bottom housing 15. Users can add appropriate amount of addition agent, such as aromatic essential oil. The appropriate amount of water in the tank 13 flows through the valve 131 to the concave groove 121 of the laminate 12 and is in contact with the atomizing device 3. After users turn on the present invention, the rotary device 4 would drive the rotary blade to rotate. The water contained in the bottom housing 15 strikes against the baffle 113 of the base and atomizes into the droplets with anions. The water in the concave groove 121 atomizes into droplets with high-frequency vibration generated by the atomizing device 3. Afterwards the air blower 2 drives the air to move. The air would carry the droplets to the exhaust cylinder 125 and further flow through the gas channel of the droplets straining device 6 to outside of the shell.

Wherein the present invention can throw and spray the water contained in the bottom housing 15 with the rotary device 4 and the rotary blade 5, so as to produce the droplets with anions. At the same time, the present invention can produce the droplets with the atomizing device 3. Therefore, in other embodiments of the present invention, if the present invention removes the atomizing device 3, the combination of the rotary device 4 and the rotary blade 5 can still serve as another atomizing device and produces the droplets. In this condition, the present invention without the atomizing device 3 can still produce droplets. To the contrary, if the present invention removes the rotary device 4 and the rotary blade 5 and keeps the atomizing device 3 therein, the atomizing device 3 can produce the droplets. In this condition, the present invention without rotary device 4 and the rotary blade 5 can still produce droplets.

The rotary blade 5 of the present invention has one or more radial recesses. Users can conveniently detach the rotary blade 5 for cleaning or repairing. Please refer to FIG. 9, because the rotary blade 5 has the radial recesses 53, when users would like to detach the rotary blade 5, they shall stretch their fingers to the radial recesses 53, thereafter the rotary blade 5 is removed from the present invention and take it down. That is, it can avoid the rotary blade 5 blocking by the baffle 113 and detaching difficultly.

Figure 8:
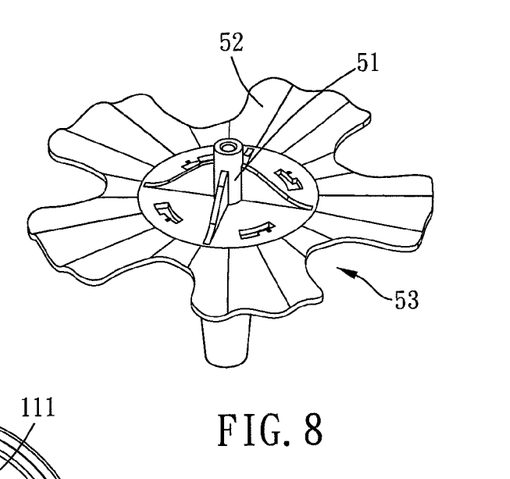
FIG. 8 is a stereogram showing a rotary blade.
Figure 9:
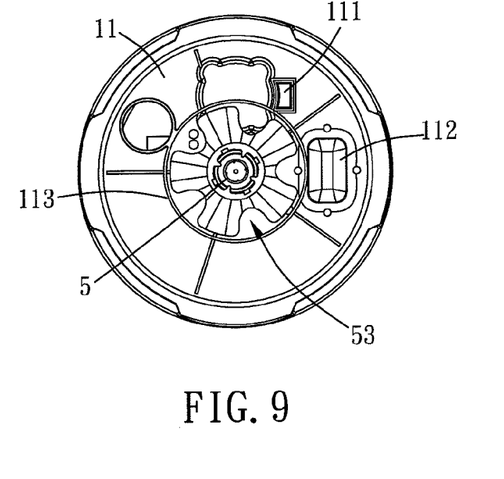
FIG. 9 is a diagram showing a rotary blade to be installed in a predetermined position.

The plate 52 of the rotary blade of the present invention can curve to wave-shaped, as shown in FIG. 8, so that the plate 52 increases its surface area. The water thrown and sprayed by the surface of the plate 52 is finer and atomizes to the drops smaller. Whereby the present invention can enhance the atomizing effect.

Accordingly, when the droplets flow with the air through the gas channel of the droplets straining device 6, due to the gas channel is roundabout and curved, some larger droplets would easily collide and adhere to the droplets straining device 6 or the exhaust cylinder 125. After the drops adhered to the droplets straining device 6 or the exhaust cylinder 125 achieve to enough weight, the drops are dripped down to the concave groove 121 of the laminate by the earth gravity. Only the smaller drops can pass through the gas channel of the droplets straining device and spray to outside of the shell. Thereby the present invention can produces and sprays water mist, which is extremely fine.

Secondly, the present invention can produce the droplets with anions by the rotary device 4 and the rotary blade 5. The drops produced by the rotary device 4 and the rotary blade 5 move to the exhaust cylinder. Thereafter the drops further combine with the droplets produced by the atomizing device 3. Wherein the smaller drops is lighter than the larger drops, so that the smaller drops are easier combine with the drops with anions than the larger drops. Relatively, some of the larger drops are easy not to carry the anions. At the moment, the droplets straining device filter and recycle the larger drops. Thereby the water mist sprayed by the present invention can carry large number of the anions and enhance the effect of the present invention.

In summary, the multifunctional Schumann wave machine of the present invention mainly adds the aromatic essential oil into water contained in the bottom housing 15. The aromatic essential oil with aromatic odor cleanses the air in the ambient environment as the rotary device 4 drive the rotary blade to rotate, and the water contained in the bottom housing 15 strikes against the baffle 113 of the base and atomizes into the droplets with anions. Users are able to breathe in droplets with anions and aromatic essential oil. Their bodies and minds are relaxed simultaneously. Note that the luminous bodies disposed around the shell, and the luminous bodies can emit different colored lights, such as red, green, blue, white, yellow, purple, etc. The luminous bodies are controlled to emit different colored lights at regular intervals or selectively emit a kind of colored lights at a time. The lights annularly go through the first and the second annular transmissive portion. Different colored lights have different relaxation effects. For instance, greenish light or yellowish light can calm down the emotion of users and has them feel better. Blue light can cure a cold if users catch it or prevent users from catching it. Purple light can comfort pregnant women. In a word, the present invention can generate different colored lights that have different levels of relaxation and placating effects for bodies and minds of users. Moreover, the lights let the ambient environment of the present invention create situations or special atmospheres at nighttime. Users are more relaxed in the situations or special atmospheres, and enjoy in the environment with aromatic essential oil, anions and colored lights. That is to say, while users use the present invention, they seem to locate in the environment which is full of sunlight (LED lights), fresh air (aromatic essential oil) and water (atomized droplets with anions), and the environment multiplies the relaxation effect for users.

It is important that the present invention can produce and spray droplets with aromatic essential oil and anions and the lights. Each luminous body releases a Schumann wave. The pulse frequency of Schumann wave is between 8 Hz and 10 Hz and penetrates through bodies of users. It can naturally adjust and neutralize the harmful electromagnetic waves radiating from electric appliances. Schumann wave is advantageous for users actually.

As such, the multifunctional Schumann wave machine of the present invention is a single mechanism, but it is able to provide three kinds of earth elements which are aroma (air), mist with anions (water) and LED colored lights (sunlight). The environment multiplies the relaxation effect for users as they use the present invention.

What is claimed is:
1. A multifunctional Schumann wave machine, comprising:

a shell, formed with a receiving space for storing water therein, the shell being formed with an air intake channel and an exhaust channel, the air intake channel and the exhaust channel communicating to the receiving space respectively, the exhaust channel having a tubular space, the shell having an annular baffle;

a luminous device, disposed around the shell, lights generated by the luminous device emitting towards outside of the shell;

a rotary device, disposed in the shell firmly;

a rotary blade, disposed on the rotary device used for driving the rotary blade to rotate, the rotary blade being located in the receiving space, and the baffle surrounding the rotary blade, so that the water in the receiving space being sprayed radially by the surface of the plate of the rotary blade and striking against the baffle to produce droplets with anions;

a droplets straining device, received in the tubular space and adapted for producing and spraying extremely fine mist;

an air blower, disposed in the shell firmly, the air blower being used for driving air via the air intake channel into the receiving space and then via the exhaust channel away from the receiving space, so that the air and the atomized water flowing through the droplets straining device to outside of the shell.

2. The multifunctional Schumann wave machine of claim 1, wherein the shell comprises a base, a laminate, and an outer housing, an outer periphery of a top portion of the base and an outer periphery of the laminate define a luminous space, the luminous device is disposed in the luminous space.

3. The multifunctional Schumann wave machine of claim 2, wherein the shell comprises a tank, the shell is formed with a receiving space therein, the receiving space further is divided into several rooms by the base, the laminate, and the tank, the luminous space does not communicate with other rooms.

4. The multifunctional Schumann wave machine of claim 2, wherein the outer periphery of the top of the base is formed with a first annular light transmissive portion, the luminous device comprises a plurality of luminous bodies, each of which has a luminous end, the luminous end faces the first annular light transmissive portion, so that lights generated by each luminous body emit through the first annular light transmissive portion to outside of the shell.

5. The multifunctional Schumann wave machine of claim 2, wherein the outer periphery of the laminate is formed with a second annular light transmissive portion, the luminous device comprises a plurality of luminous bodies, each of which has a luminous end, the luminous end faces the second annular light transmissive portion, so that lights generated by each luminous body emit through the second annular light transmissive portion to outside of the shell.

6. The multifunctional Schumann wave machine of claim 1, wherein the rotary blade has a rotation axle and a plate, the plate extends from the rotation axle radially, the plate has an outer periphery tortuously formed with at least a radial recess.

7. The multifunctional Schumann wave machine of claim 1, wherein the droplets straining device comprises a rod and a division plate assembly, the division plate assembly extends from the rod radially, the droplets straining device is received in the tubular space, an outer periphery of the division plate assembly away from the rod abuts a periphery of the tubular space, the division plate defines the tubular space into a gas channel, the gas channel extending non-linearly.

8. The multifunctional Schumann wave machine of claim 1, further comprising an atomizing device disposed in the shell firmly and located in the receiving space, the atomizing device being capable of generating vibration to atomize the water in the receiving space.

9. The multifunctional Schumann wave machine of claim 1, wherein each luminous body releases a Schumann wave, the pulse frequency of Schumann wave is between 8 Hz and 10 Hz.

\* \* \* \* \*